US00PP22781P2

(12) United States Plant Patent
Moore

(10) Patent No.: US PP22,781 P2
(45) Date of Patent: Jun. 12, 2012

(54) STRAWBERRY PLANT NAMED 'PUGET CRIMSON'

(50) Latin Name: ***Fragaria×ananassa* Duch**
Varietal Denomination: Puget Crimson

(75) Inventor: Patrick P. Moore, Puyallup, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 12/931,592

(22) Filed: Feb. 3, 2011

(51) Int. Cl.
*A01H 5/00* (2006.01)

(52) U.S. Cl. ..... Plt./208

(58) Field of Classification Search ..... Plt./208
See application file for complete search history.

*Primary Examiner* — Annette Para
(74) *Attorney, Agent, or Firm* — Michelle Bos

(57) ABSTRACT

This invention relates to a new and distinct cultivar of strawberry plant (*Fragaria×ananassa* Duch) named 'Puget Crimson'. 'Puget Crimson' is a late season, June-bearing (short-day) cultivar adapted to the Pacific Northwest. 'Puget Crimson' is distinguished by its upright growth habit, strong vigor, large fruit that is longer than wide, high yields of very late season production and an excellent strong strawberry flavor.

5 Drawing Sheets

FEDERALLY SPONSORED RESEARCH OR DEVELOPMENT

The invention was made in part with Federal formula funds pursuant to the Hatch Act and was part of Project WNP0038. The United States Government has certain rights in the invention.

Genus and species: *Fragaria×ananassa* Duch.
Variety denomination: 'Puget Crimson'.

BACKGROUND OF THE INVENTION

This invention relates to a new and distinct June-bearing (short day) strawberry cultivar designated as 'Puget Crimson', which resulted from a hand pollinated cross of 'Schwartze' and 'Valley Red' made in 2003 at the Washington State University Puyallup Research and Extension Center, Puyallup, Wash. 'Schwartze' (U.S. Plant Pat. No. 12,067) is a late season, short day, fresh market cultivar that is marketed under the name 'Puget Summer'. 'Valley Red' (not patented) is an early season, short day cultivar primarily suited to processing with dark interior and exterior color.

'Puget Crimson' was selected in 2005 at the Washington State University Puyallup Research and Extension Center Roy Goss Farm at Puyallup, Wash., and was propagated asexually by runners (stolons) and by tissue culture. The selection was tested as WSU 2833. Asexually propagated propagules from this original source have been tested at the Roy Goss Farm and to a limited extent in grower fields.

SUMMARY OF THE INVENTION

'Puget Crimson' is distinguished by fruit that is large, firm, and easily capped, with excellent flavor. Fruit is produced very late in the June-bearing season. 'Puget Crimson' is well adapted to a perennial, matted-row production system in the Pacific Northwest.

The new and distinct cultivar of strawberry originated from a hand-pollinated cross of 'Schwartze'×'Valley Red' made in 2003 in Puyallup, Wash. 'Schwartze' is marketed under the name 'Puget Summer' and is a short-day cultivar that produces conical, firm, easily capped fruit with excellent flavor very late in the June-bearing season. Fruit produced early in the season is large, but later fruit can be much smaller and fruit in the second fruiting season is medium to small in size. Most of the fruit of 'Schwartze' is held up off the ground during fruit development. Plants of 'Schwartze' are very vigorous, but are very susceptible to powdery mildew. 'Valley Red' is an early season short-day plant that produces medium to large sized fruit that is conic in shape with good uniformity in size and shape.

Seeds resulting from the controlled hybridization of 'Schwartze' and 'Valley Red' were germinated in a greenhouse in Puyallup, Wash. in 2003-04 and planted at the Roy Goss Farm in spring 2004. The seedlings fruited in the summer of 2005 and one seedling, designated WSU 2833, was selected for its attractive, large fruit with excellent flavor and late ripening season. The original plant selection was propagated asexually by runners (stolons) and using tissue culture at Puyallup, Wash. and a test planting of eight plants was established in 2006. This planting was harvested in 2007 and 2008, and WSU 2833 had high yields of very large, excellent flavored fruit. Based on its 2007 performance, WSU 2833 was planted in three replications of eight plants in 2008 and 2009 at the Roy Goss Farm. The combination of traits disclosed herein that characterize 'Puget Crimson' have been retained true to type through successive cycles of asexual propagation.

The following list of traits in combination define the new cultivar as a unique cultivar distinguishing it from other commercial short day strawberries in the region:

upright growth habit, strong vigor
large, longer than wide, conic- to wedge-shaped fruit
red to dark red fruit, both exterior and interior
excellent strong strawberry flavor
very late season production with high yields.

'Puget Crimson' is distinguished from 'Schwartze' by larger fruit size in 'Puget Crimson', especially in the second fruiting season. The color of both the upper and lower surfaces of the leaves of 'Puget Crimson' differ from 'Schwartze' by 'Puget Crimson' having greater chroma values in Munsell notation. The proportion of the leaf margin with serrations is less on 'Puget Crimson' than on 'Schwartze'.

'Puget Crimson' is distinguished from 'Valley Red' by having a much later ripening period for 'Puget Crimson' and a greater fruit length to width ratio for 'Puget Crimson'.

'Puget Crimson' is distinguished from 'Puget Reliance' (U.S. Plant Pat. No. 9,310) by having a much later ripening period for 'Puget Crimson'.

BRIEF DESCRIPTION OF THE DRAWINGS

The accompanying photographs show typical specimens of the new cultivar, in color as nearly true as it is reasonably possible to make in color illustrations of this character. Photographs are intended to show morphological features of the plant.

DETAILED BOTANICAL DESCRIPTION

When objects could be accurately measured with an 8 mm diameter measuring opening (leaves and fruit), color was measured with a Minolta Chroma Meter CR-400, which measures color in L*, a*, b* color coordinates. Calibration was performed using a standard white plate supplied by the manufacturer. These L*, a*, b* coordinates were converted and are presented in Munsell color notation. For all other color measurements, color was compared with Royal Horticultural Society Colour Chart color plates and presented as Royal Horticultural Society Colour Chart, London designations (R.H.S.).

The descriptions reported herein are from specimens grown at Puyallup, Wash., unless otherwise noted. The characteristics of the new cultivar may vary in detail, depending on variations in environmental factors, such as temperature, rainfall, humidity and light intensity. 'Puget Crimson' has not been observed under all possible environmental conditions.

Fruit, Fruit Production and Fruit Quality Characteristics

Figure 1:
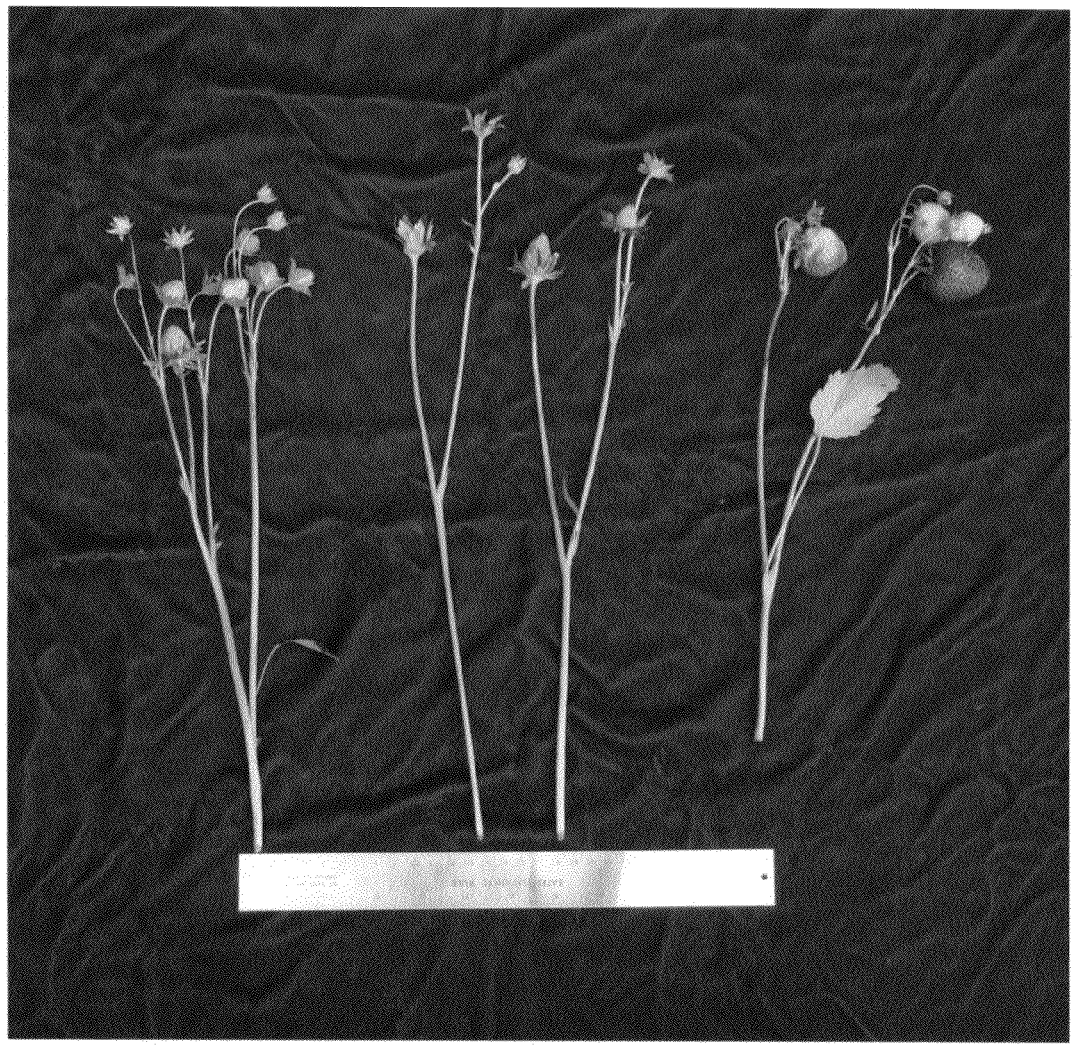
FIG. 1 shows the fruiting truss structure of A) 'Firecracker' (not patented); B) 'Puget Crimson'; and C) 'Valley Red' on Jun. 15, 2010.

Fruiting trusses were collected for 'Puget Crimson', 'Firecracker' and 'Valley Red' on Jun. 14, 2010 (FIG. 1). 'Puget Crimson' had a peduncle diameter of 3.7 mm and a fruiting truss length of 43 cm (Table 1). There were no differences among cultivars for pedicle diameter and total length. The total number of flower buds and the number of open flowers, green fruit and red fruit per peduncle were counted. 'Puget Crimson' had a total of 3.0 buds, flowers or fruit, while 'Firecracker' averaged 8.2 and 'Valley Red' averaged 6.2. The stage of development was much further advanced for 'Valley Red' than for 'Puget Crimson' with 32% red fruit for 'Valley Red' and 0% for 'Puget Crimson'.

TABLE 1

Fruiting truss measurements made Jun. 13, 2010

| | Peduncle diameter (mm) | | Fruiting truss length (cm) | | Total number of buds/flowers/fruit per fruiting truss | | Number of red fruit per fruiting truss | |
|---|---|---|---|---|---|---|---|---|
| Puget Crimson | 3.7 | a | 42.8 | a | 3.0 | b | 0.0 | a |
| Valley Red | 4.0 | a | 39.8 | a | 6.2 | a | 2.0 | a |
| Firecracker | 3.8 | a | 38.8 | a | 8.2 | a | 0.0 | b |

Peduncle diameter measured 2.5 cm from the base of the peduncle.
Means based on 5 fruiting trusses per clone.
Means followed by the same letter within a column are not significantly different using Tukey's Studentized Range (HSD) Test, P = 0.05.

Bloom for 'Puget Crimson' began about the week of May 17 in 2010 and a few blooms were still present Jun. 27, 2010. The timing of the bloom period of 'Puget Crimson' is very similar to 'Firecracker' and 'Schwartze'.

Figure 2:
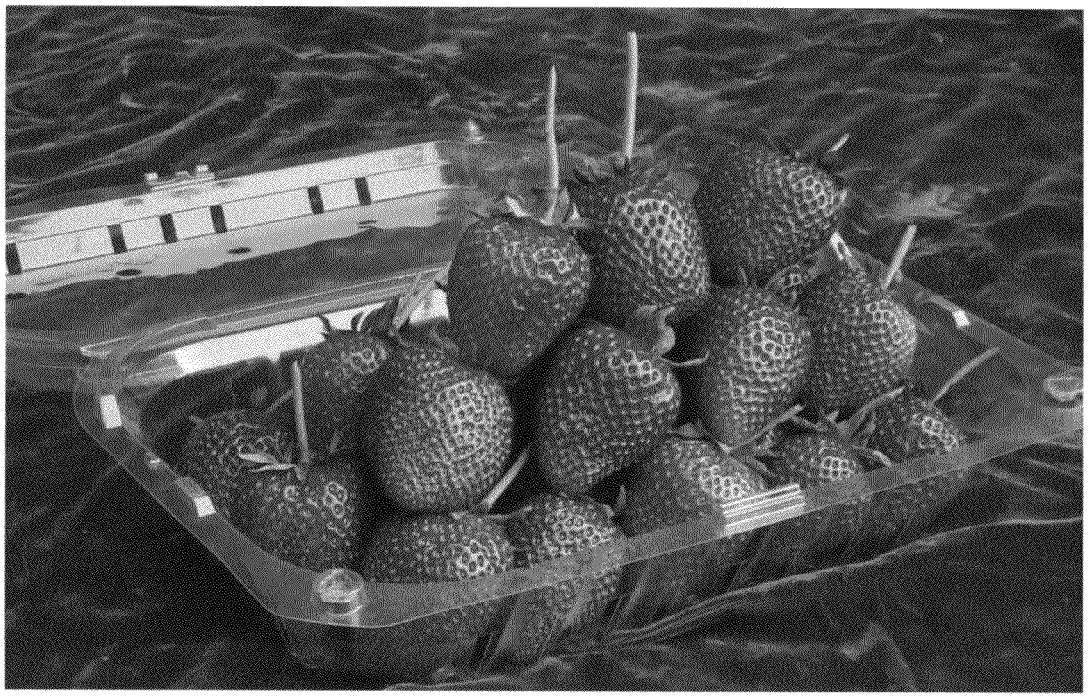
FIG. 2 shows typical fruit shape and uniformity of early season fruit of 'Puget Crimson' on Jun. 22, 2010.

Fruit of 'Puget Crimson', 'Firecracker' and 'Schwartze' harvested Jul. 9, 2010 were measured (Table 2). Fruit of 'Schwartze' was smaller than that of 'Puget Crimson' and 'Firecracker'. The length of 'Puget Crimson' fruit was longer than either 'Firecracker' or 'Schwartze'. The length to width ratio for 'Puget Crimson' was greater than that of 'Firecracker'. Fruit of 'Puget Crimson' harvested on Jul. 9, 2010 were large, glossy, attractive and uniform (FIG. 2).

TABLE 2

Fruit measurements made Jul. 9, 2010

| | Fruit weight (g) | | Fruit length (mm) | | Fruit width (mm) | | Length/ width ratio | | Fruit color Exterior | Fruit color Interior | Calyx diameter (mm) | |
|---|---|---|---|---|---|---|---|---|---|---|---|---|
| Puget Crimson | 17.2 | a | 40.5 | a | 33.0 | a | 1.23 | a | 7.5R 3/8 | 10R 5/10 | 30.2 | a |
| Firecracker | 17.3 | a | 33.5 | b | 33.1 | a | 1.02 | b | 7.5R 3/7 | 10R 5/10 | 30.8 | a |
| Schwa rtze | 13.4 | b | 34.8 | b | 29.3 | b | 1.20 | ab | 5R 3/7 | 10R 5/10 | 27.8 | a |

Means based on 5 fruit per clone.
Color measured with a Minolta CR-400 colorimeter as L*, a*, b* values and converted to Munsell values.
Exterior measurements of color were taken at the shoulder of the fruit. Interior measurements of color were taken at the distal point of a transverse section of the fruit.
Means followed by the same letter within a column are not significantly different using Tukey's Studentized Range (HSD) Test, P = 0.05.

Fruit was harvested in 2009 and 2010 from replicated plots of 'Puget Crimson' and other Pacific Northwest cultivars planted June 2008 (Table 3). In 2009, 'Puget Crimson' had the greatest yield, although there were no significant differences among cultivars. In 2010, 'Puget Reliance', 'Tillamook' and 'Puget Crimson' had the greatest yield. 'Puget Crimson' and 'Tillamook' had the largest fruit in both years. 'Tillamook' and 'Puget Crimson' had the firmest fruit in 2009, but differed significantly only from 'Hood' and 'Puget Reliance'. In 2010, fruit firmness of 'Puget Crimson', 'Firecracker' and 'Tillamook' was reduced because of weather conditions late in the season. The midpoint of harvest for 'Puget Crimson' and 'Firecracker' were significantly later than for other Pacific Northwest cultivars in both years.

TABLE 3

2009-2010 harvest data for 2008 planted strawberries, Puyallup, Washington.

| | Yield (t/a) | | | | | | Fruit Rot (%) | | | |
|---|---|---|---|---|---|---|---|---|---|---|
| | 2009 | | 2010 | | Total | | 2009 | | 2010 | |
| Puget Crimson | 12.8 | a | 17.0 | ab | 29.8 | ab | 14.5 | a | 20.4 | ab |
| Firecracker | 9.3 | a | 10.7 | bc | 20.0 | bc | 6.3 | a | 23.7 | ab |
| Hood | 10.8 | a | 7.0 | c | 17.8 | c | 10.9 | a | 29.7 | a |
| Puget Reliance | 12.5 | a | 19.8 | a | 32.4 | a | 19.7 | a | 12.9 | b |
| Tillamook | 8.3 | a | 18.6 | a | 26.9 | a-c | 10.7 | a | 13.4 | b |
| Totem | 9.4 | a | 11.2 | bc | 20.6 | bc | 11.2 | a | 20.0 | ab |

| | Fruit weight (g) | | | | Fruit firmness (g) | | | |
|---|---|---|---|---|---|---|---|---|
| | 2009 | | 2010 | | 2009 | | 2010 | |
| Puget Crimson | 15.0 | a | 16.8 | ab | 210 | a | 156 | b |
| Firecracker | 14.9 | a | 11.3 | d | 205 | a | 149 | b |
| Hood | 12.2 | a | 12.1 | cd | 177 | b | 184 | ab |
| Puget Reliance | 12.8 | a | 14.8 | bc | 176 | b | 164 | b |
| Tillamook | 15.1 | a | 18.7 | a | 211 | a | 175 | b |
| Totem | 12.3 | a | 12.0 | cd | 199 | ab | 212 | a |

| | 2009 | | | | | | | |
|---|---|---|---|---|---|---|---|---|
| | Dates for percent cumulative yield | | | | | | Length of harvest | |
| | 5% | | 50% | | 95% | | season (d) | |
| Puget Crimson | 6/16 | a | 6/25 | a | 7/11 | a | 25 | a |
| Firecracker | 6/13 | a | 6/23 | ab | 7/2 | b | 19 | b |
| Puget Reliance | 6/8 | b | 6/19 | bc | 6/29 | b | 21 | ab |
| Tillamook | 6/9 | b | 6/18 | bc | 6/29 | b | 20 | b |
| Hood | 6/9 | b | 6/16 | c | 6/27 | b | 19 | b |
| Totem | 6/9 | b | 6/16 | c | 6/27 | b | 19 | b |

| | 2010 | | | | | | | |
|---|---|---|---|---|---|---|---|---|
| | Dates for percent cumulative yield | | | | | | Length of harvest | |
| | 5% | | 50% | | 95% | | season (d) | |
| Puget Crimson | 6/27 | a | 7/8 | a | 7/18 | a | 21 | a |
| Firecracker | 6/28 | a | 7/8 | a | 7/19 | a | 20 | a |
| Puget Reliance | 6/15 | c | 6/26 | c | 7/7 | c | 22 | a |
| Tillamook | 6/20 | b | 6/30 | b | 7/12 | b | 22 | a |
| Hood | 6/13 | c | 6/24 | c | 7/4 | c | 21 | a |
| Totem | 6/15 | c | 6/25 | c | 7/3 | c | 18 | a |

Values represent means of three replications of 10 foot plots.

Fruit firmness was measured as the force required for a 4-mm diameter cylinder to penetrate the shoulder of a fruit to a depth of 6 mm. Firmness was measured using a Hunter Spring mechanical force gauge (series L; Amtec, Hatfield, Pa) for five fruit per plot at each harvest. The weighted mean was calculated for the harvest season.

Means followed by the same letter within a column are not significantly different using Tukey's Studentized Range (HSD) Test, P = 0.05.

Although 'Schwartze' was not included in the 2009 planting, it has been included in five plantings at Puyallup, Wash. that were harvested for two seasons since 1996. The average fruit weight for 'Schwartze' in the first harvest season for these plantings was 14.9 g with a range of 11.9 g (1998 planting harvested in 1999) to 16.4 g (2003 planting harvested in 2004). In the second harvest season, the average fruit weight for 'Schwartze' was 9.5 g with a range of 7.3 g (1996 planting harvested in 1998) to 10.7 g (2001 planting harvested in 2003). In the planting established in 1996, the fruit weight of 'Schwartze' in the first harvest season (1997) was 15.8 g and in the second season (1998) was 7.3 g, less than 50% of the first season. The fruit weight of 'Puget Crimson' in the 2008 planting was 15.0 g in the first harvest season and increased numerically to 16.8 g in the second harvest season (Table 3). The fruit weight of 'Puget Crimson' in the second harvest season is much larger than 'Schwartze' in a second harvest season.

'Puget Crimson' was compared to other cultivars including 'Valley Red' for harvest characteristics in plots established June 2009 (Table 4). The most distinct difference was the ripening season for 'Puget Crimson' and 'Valley Red'. The midpoint of harvest for 'Puget Crimson' in 2010 was Jul. 5, 2010 while that for 'Valley Red' was June 12. This is also demonstrated in FIG. 2 which shows differences in flower and fruit development between 'Puget Crimson' and 'Valley Red' on Jun. 15, 2010.

TABLE 4

2010 harvest of 2009 planted strawberries, Puyallup, Washington.

| | Yield (t/a) | | Fruit rot (%) | | Fruit weight (g) | | Fruit firmness (g) | |
|---|---|---|---|---|---|---|---|---|
| Puget Crimson | 13.7 | a | 10.5 | ab | 15.8 | a-c | 170 | b |
| Tillamook | 8.3 | b | 9.2 | ab | 18.9 | a | 218 | a |
| Valley Red | 8.2 | b | 10.0 | ab | 17.2 | ab | 213 | a |
| Puget Reliance | 7.2 | b | 5.6 | b | 14.2 | a-c | 219 | a |
| Totem | 6.7 | b | 9.8 | ab | 11.3 | c | 247 | a |
| Hood | 6.6 | b | 15.4 | a | 11.4 | bc | 218 | a |

| | Dates for percent cumulative yield | | | | | | Length of harvest | |
|---|---|---|---|---|---|---|---|---|
| | 5% | | 50% | | 95% | | season (d) | |
| Puget Crimson | 6/22 | a | 7/5 | a | 7/18 | a | 25 | a |
| Tillamook | 6/11 | b | 6/24 | b | 7/5 | b | 23 | ab |
| Valley Red | 6/5 | c | 6/12 | c | 6/25 | c | 21 | b |
| Puget Reliance | 6/10 | b | 6/24 | b | 7/4 | b | 24 | ab |
| Totem | 6/9 | b | 6/23 | b | 7/3 | b | 24 | ab |
| Hood | 6/9 | b | 6/23 | b | 7/3 | b | 24 | ab |

Values represent means of three replications of 10 foot plots.

Fruit firmness was measured as the force required for a 4-mm diameter cylinder to penetrate the shoulder of a fruit to a depth of 6 mm. Firmness was measured using a Hunter Spring mechanical force gauge (series L; Amtec, Hatfield, Pa) for five fruit per plot at each harvest. The weighted mean was calculated for the harvest season.

Means followed by the same letter within a column are not significantly different using Tukey's Studentized Range (HSD) Test, P = 0.05.

The fruit storage effects on 'Puget Crimson' were compared to two other late-season cultivars for fruit harvested Jun. 9, 2010. Fruit was harvested, the fruit weighed and color measured and then the fruit were placed in individual containers and stored for 4 days at 4° C. After 4 days, the fruit was moved to room temperature (approximately 20° C.) for 4 hours and then the same fruit measured a second time. There were no differences among cultivars in the amount of weight lost, but 'Puget Crimson' had the lowest percentage weight loss (Table 5). Color after storage was similar for all cultivars. 'Puget Crimson' had acceptable storage characteristics.

TABLE 5

Changes in fruit weight and color during storage

| | Fruit weight (g) | | | | | | | | Exterior fruit color | |
|---|---|---|---|---|---|---|---|---|---|---|
| | | | | | Weight | | | | | |
| | Into storage | | After storage | | loss (g) | | Weight loss (%) | | Into storage | After storage |
| Puget Crimson | 16.17 | a | 15.72 | a | 0.45 | a | 2.83 | c | 7.5R 3/8 | 5R 3/7 |
| Firecracker | 13.97 | b | 13.40 | b | 0.58 | a | 4.16 | b | 7.5R 3/7 | 5R 3/7 |
| Schwartze | 10.77 | c | 10.18 | c | 0.58 | a | 5.51 | a | 5R 3/6 | 5R 3/6 |

Values represent means of 12 samples per clone.

Fruit harvested Jul. 9, 2010, data collected on individual fruit, then stored in individual containers at 4° C. for 4 days, then stored at room temperature (approximately 20° C.) for 4 hours and the same fruit measured a second time.

Color measured with a Minolta CR-400 colorimeter as L*, a*, b* values and converted to Munsell values.

Means followed by the same letter within a column are not significantly different using Tukey's Studentized Range (HSD) Test, P = 0.05.

Fruit samples of 'Puget Crimson' and two other late-season cultivars were collected in 2010 and analyzed for soluble solids, titratable acidity, pH, total anthocyanins and total phenolics (Table 6). 'Puget Crimson' and 'Firecracker' had comparable levels of soluble solids, which were lower than those of 'Schwartze'. Measurements of pH for 'Puget Crimson' were intermediate between the two cultivars. 'Puget Crimson' and 'Firecracker' have similar total anthocyanin levels and both are less than 'Schwartze'.

TABLE 6

Analysis of strawberry fruit harvested Jul. 12, 2010, Puyallup, Washington

| Clone | Soluble Solids (° brix) | | pH | | Titratable acidity (g citric acid/100 g) | | Total anthocyanins (mg Pg-3-G/ 100 g) | | Total phenolics (mg GAE/ 100 g) | |
|---|---|---|---|---|---|---|---|---|---|---|
| Puget Crimson | 9.8 | b | 3.62 | b | 0.88 | c | 57.5 | b | 294 | c |
| Firecracker | 9.6 | b | 3.45 | c | 1.17 | a | 54.3 | b | 321 | b |
| Schwartze | 12.9 | a | 3.77 | a | 1.02 | b | 89.2 | a | 352 | a |

Analyses were performed on fruit samples of 175-275 g fresh weight. Values represent means of three replications.

Soluble solids were measured using a PAL-1 digital handheld refractometer (Atago USA, Bellevue, WA)

Titratable acidity, total anthocyanins and total phonolics expressed on a fresh weight basis.

Total anthocyanins were measured as pelargonidin-3-glucoside (Pg-3-G)

Total phenolics were measured as gallic acid equivalents (GAE)

Means followed by the same letter within a column are not significantly different using Fisher's Protected least significant differences test, P = 0.05.

Detailed flower and fruit characteristics of 'Puget Crimson':

*Color of petals.*—155D (RHS white group).

*Shape of petals.*—Orbicular to oval; width equal or slightly less than length.

*Number of petals.*—Usually five, occasionally six.

*Flower fragrance.*—None detected.

*Color of calyx.*—147B (RHS yellow green group).

*Size of calyx relative to fruit diameter.*—Smaller.

*Attitude of calyx segments.*—Most fruit with reflexed calyx segments.

*Adherence of calyx (when fully ripe).*—Easily removed.

*Color of fruit surface.*—Bright to dark red 7.5R 3/8 (Munsell).

*Color of flesh.*—Medium red 10R 5/10 (Munsell) measured at the distal point of a transverse section of the fruit.

Figure 3:
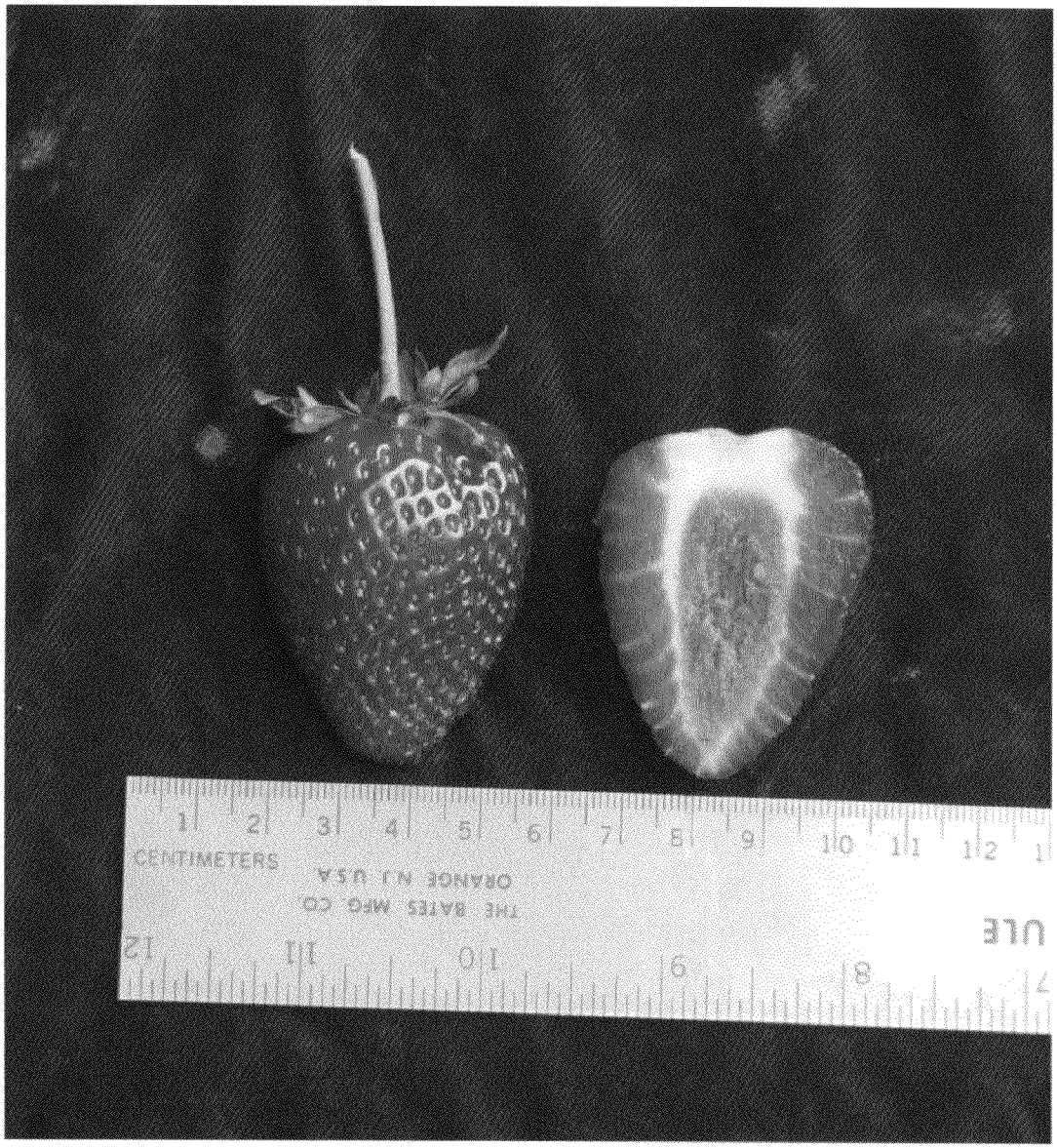
FIG. 3 shows typical external and internal fruit characteristics of 'Puget Crimson' including calyx structure and fruit shape on Jun. 22, 2010.

*Distribution of red color of the flesh.*—There may be a lighter ring around the central core of the fruit and the connections to the achenes are white (FIG. 3). As fruit continues to ripen the light portions of the flesh become darker.

*Color under calyx.*—Surface is red except for area immediately around where calyx attaches to the fruit.

*Achene distribution.*—Achenes are present under the calyx segments, but not immediately around where calyx attaches to the fruit.

*Ratio of length/width.*—Longer than wide.

*Neck.*—The fruit does not display a neck.

*Size.*—Large to very large.

*Shape.*—Mostly conical with few wedge shaped.

*Glossiness.*—Moderate.

*Insertion of achenes.*—Level to slightly recessed.

*Achene color.*—16A (RHS yellow-orange group) for light colored fruit to 58B (RHS red-purple group) when fully ripe.

*Hollow center.*—Primary fruit usually have a hollow center that becomes smaller or disappears with later fruit.

*Time of flowering.*—Very late.

*Fruiting season.*—Very late.

*Type of bearing.*—Short day type.

Plant Size

Figure 4:
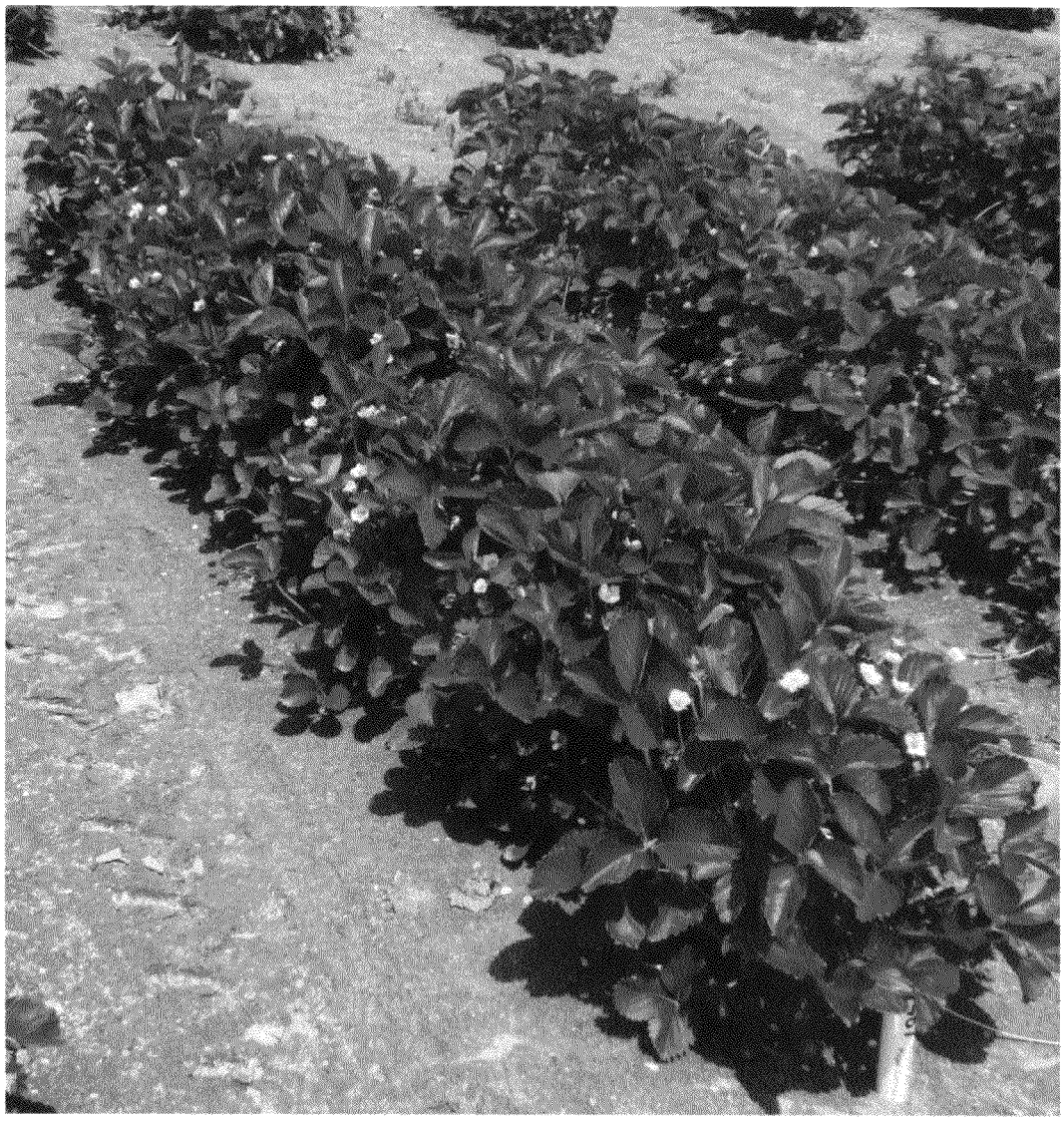
FIG. 4 shows a typical plot of 'Puget Crimson' planted in June 2008, showing the vigor of the plant and the flowers at or below the leaf canopy level on Jun. 2, 2009.

The plants of 'Puget Crimson' are large and vigorous. It produces abundant runners and forms a very dense matted row with a dense canopy (FIG. 4). Plots of 'Puget Crimson' and 'Firecracker' established in June 2008 were measured Jun. 27, 2010. 'Puget Crimson' plants had a width of 93 cm and a height of 48 cm. 'Firecracker' plants had a width of 83 cm and height of 48 cm.

Figure 5:
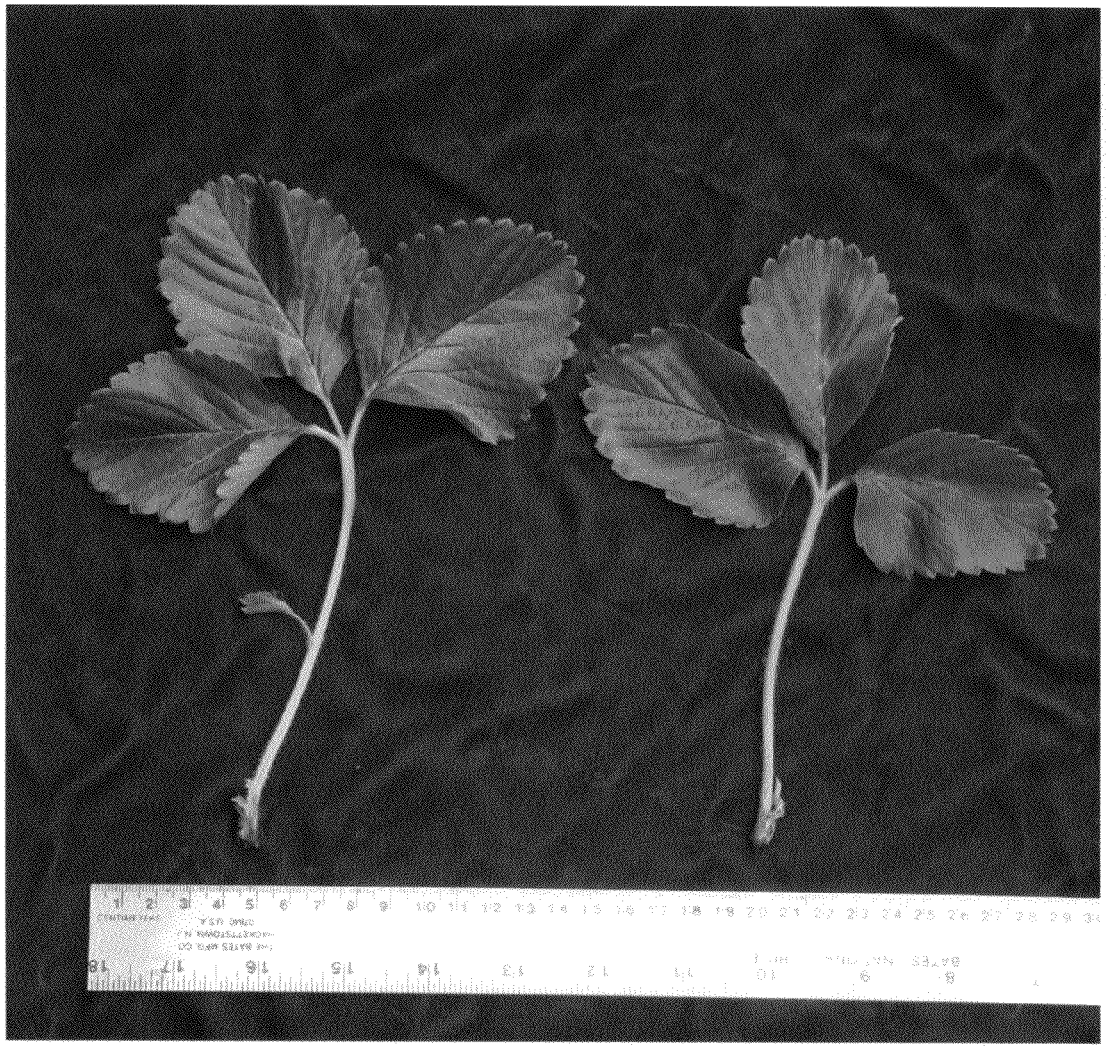
FIG. 5 shows typical leaves of 'Puget Crimson' on Sep. 3, 2010 with the leaf on the left showing a bract leaflet.

The leaves of 'Puget Crimson' are shown in FIG. 5. Leaves were collected for measurements from plots established in June 2009 (Table 7). Fruit in these plots were harvested June to July 2010 and the plots then renovated in late July. This is a standard practice for matted row production in the Pacific Northwest where plantings are harvested for several years. The leaves measured were produced between renovation and Sep. 3, 2010 when the leaves were collected. Leaves of 'Puget Crimson' and 'Valley Red' were similar, differing significantly only in the number of serrations on the terminal leaflet. Plants of 'Schwartze' were in this planting, but plant establishment was poor and leaf size was abnormally small and were not included in the leaf size measurements. The leaves of 'Schwartze' in this planting were included in color measurements. The color of both the upper and lower surfaces of the leaves of 'Puget Crimson' differ from 'Schwartze' with 'Puget Crimson' having higher chroma values in Munsell notation. The proportion of the leaf margin with serrations is less on 'Puget Crimson' than on 'Schwartze'.

TABLE 7

Comparison of leaf characteristics of Puget Crimson with its parents.

| | Puget Crimson | | Valley Red | | Schwartze |
|---|---|---|---|---|---|
| Petiole length (cm) | 12.3 | a | 13.1 | a | — |
| Petiole diameter (mm) | 2.9 | a | 2.8 | a | — |
| Petiolule length of terminal leaflet (mm) | 10.3 | a | 9.3 | a | — |
| Terminal leaflet length (mm) | 67.5 | a | 69.4 | a | — |
| Terminal leaflet width (mm) | 53.6 | a | 53.2 | a | — |
| Length/width ratio | 1.26 | ab | 1.31 | a | — |
| Number of serrations | 20.4 | a | 18.1 | b | — |

TABLE 7-continued

Comparison of leaf characteristics of Puget Crimson with its parents.

| | Puget Crimson | Valley Red | Schwartze |
|---|---|---|---|
| Proportion of leaf margin with serrations (%) | 60 | 61 | 69 |
| Leaf color upper surface | 6.5GY 3.6/3.8 | 6.5GY 3.6/3.9 | 6.3GY 3.6/3.4 |
| Leaf color lower surface | 6.0GY 5.2/3.5 | 6.0GY 5.2/3.4 | 6.3GY 5.2/3.0 |

Values represent means of 15 samples collected Sep. 3, 2010 for each clone from plots established June 2009. Plots were harvested June to July 2010, then renovated by leaf removal at the end of July 2010. Leaves measured were produced between renovation and Sep. 3, 2010.
Petiole diameter measured 2.5 cm from the base of the petiole.
Color measured with a Minolta CR-400 colorimeter as L*, a*, b* values and converted to Munsell values.
Means followed by the same letter within a column are not significantly different using Tukey's Studentized Range (HSD) Test, P = 0.05.

Comparative Plant Characteristics

Detailed plant characteristics of 'Puget Crimson':

*Size*.—Large.

*Habit*.—Upright.

*Density*.—High.

*Vigor*.—Strong.

*Height*.—Tall.

*Spread*.—Wide.

Detailed foliage characteristics of 'Puget Crimson':

*Color of upper surface of leaves*.—6.3GY 3.6/3.4 (Munsell).

*Color of lower surface of leaves*.—6.3GY 5.2/3.4 (Munsell).

*Shape of cross section*.—Concave.

*Number of leaflets*.—Three.

*Terminal leaflet*.—Size — medium; length/width ratio — longer than wide; shape of base — cunate; shape of serrations — acute; number of serrations — 20; proportion of leaf margin with serrations — approximately 60%; The angle between the terminal leaflet base and the petiolule is approximately 130° .

*Petiole*.—Pubescence density — moderate; color 145A (RHS yellow green group); attitude of hairs — generally toward base of petiole, but often at 90° to the axis of the petiole; size of bract leaflets — small; frequency of bract leaflets — occur on approximately 20% of petioles.

Disease Resistance

Similar to its parent 'Schwartze', 'Puget Crimson' is susceptible to the powdery mildew [*Spherotheca macularis* (Wallr. Ex. Rg.)] and moderately susceptible to leaf scorch (*Diplocarpon*).

I claim:

1. A new and distinct variety of strawberry plant, as illustrated and described herein.

* * * * *